US009591977B2

(12) United States Patent
Xue et al.

(10) Patent No.: US 9,591,977 B2
(45) Date of Patent: Mar. 14, 2017

(54) METHOD AND APPARATUS FOR COMPARING AND VISUALIZING SERIAL ECG DATA

(71) Applicant: General Electric Company, Schenectady, NY (US)

(72) Inventors: Joel Qiuzhen Xue, Wauwatosa, WI (US); Brian J. Young, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 162 days.

(21) Appl. No.: 14/587,704

(22) Filed: Dec. 31, 2014

(65) Prior Publication Data

US 2016/0183827 A1  Jun. 30, 2016

(51) Int. Cl.
*A61B 5/04* (2006.01)
*A61B 5/0408* (2006.01)
*A61B 5/044* (2006.01)
*A61B 5/0452* (2006.01)

(52) U.S. Cl.
CPC .......... *A61B 5/04012* (2013.01); *A61B 5/044* (2013.01); *A61B 5/0452* (2013.01); *A61B 5/04085* (2013.01)

(58) Field of Classification Search
CPC ... A61B 5/044; A61B 5/04012; A61B 5/0452; A61B 5/04085

USPC ......................................................... 600/523
See application file for complete search history.

(56) References Cited

U.S. PATENT DOCUMENTS

2015/0005651 A1* 1/2015 Vellani ............... A61B 5/04011
                                                    600/512

* cited by examiner

*Primary Examiner* — Amanda Patton
*Assistant Examiner* — Philip C Edwards
(74) *Attorney, Agent, or Firm* — Andrus Intellectual Property Law LLP (57) ABSTRACT

A method of analyzing electrocardiograph (ECG) data includes receiving a first representative ECG of a patient and isolating a first principal component, a second principal component, and a third principal component of the first representative ECG. The principal components are isolated by selecting a portion of the first representative ECG relating to depolarization, calculating a covariance matrix based on the portion of the first representative ECG, conducting a principal component analysis of the covariance matrix, and selecting a first component of the principal component analysis as the first principal component, the second component of the principal component analysis as the second principal component, and the third component of the principal component analysis as the third principal component. A depolarization subspace is then formed based on the first principal component, second principal component, and the third principal component of the first representative ECG.

20 Claims, 7 Drawing Sheets

METHOD AND APPARATUS FOR COMPARING AND VISUALIZING SERIAL ECG DATA

BACKGROUND

The present disclosure relates generally to cardiac monitoring methods and techniques, and more specifically to a method and apparatus for analyzing cardiac waveforms recorded by an electrocardiograph (ECG).

Electrocardiograph (ECG) monitoring is a standard method of monitoring, assessing, and diagnosing patient cardiac health. Patient care often involves recording multiple ECGs from a patient. For example, ECGs may be taken at regular intervals, such as during patient checkups, and repetitive ECGs may be recorded from a patient while a patient is being treated for a health condition. For example, when treating a patient for a cardiac condition, multiple ECG recordings may be made for the patient over a period of time. In order to thoroughly assess such serial ECG recordings, clinicians need to compare the recordings to one another in order to detect any significant cardiac changes in a patient.

SUMMARY

In one embodiment, a method of analyzing electrocardiograph (ECG) data includes receiving a first representative ECG of a patient and isolating a first principal component, a second principal component, and a third principal component of the first representative ECG. The principal components are isolated by selecting a portion of the first representative ECG relating to depolarization, calculating a covariance matrix based on the portion of the first representative ECG, conducting a principal component analysis of the covariance matrix, and selecting a first component of the principal component analysis as the first principal component, the second component of the principal component analysis as the second principal component, and the third component of the principal component analysis as the third principal component. A depolarization subspace is then firmed based on the first principal component, second principal component, and the third principal component of the first representative ECG.

Another embodiment of a method of comparing serial ECG data includes forming a depolarization subspace based on a first principal component, a second principal component, and a third principal component of the first representative ECG and then projecting a second representative ECG to the depolarization subspace to isolate at least a first aligned component and a second aligned component of the second representative ECG. The depolarization subspace is formed by calculating a covariance matrix based on a portion of the first representative ECG relating to depolarization of a patient's heart, conducting a principal component analysis of the covariance matrix and selecting a first component of the principal component analysis as the first principal component, the second component of the principal component analysis as a second principal component and a third component of the principal component analysis as the third principal component. The second representative ECG is based on ECG data recorded from the patient at a different time than the first representative ECG. Furthermore, the first aligned component is on the same axis as the first principal component and the second aligned component is on the same axis as the second principal component.

One embodiment of a computer program product for detecting a cardiac change in a patient includes a first program product portion configured to form a depolarization subspace based on a first principal component, a second principal component, and a third principal component of a first representative ECG. The first program product portion is configured to calculate a covariance matrix based on a portion of the first representative ECG relating to depolarization of a patient's heart, conduct a principal component analysis of the covariance matrix, and select the first component of the principal component analysis as the first principal component, the second component of the principal component analysis as the second principal component, and the third component of the principal component analysis as the third principal component. A second program product portion is configured to project a second representative ECG to the depolarization subspace to isolate at least a first aligned component and a second aligned component of the second representative ECG, wherein the first aligned component is on the same axis as the first principal component and the second aligned component is on the same axis as the second principal component. A third program product portion is configured to compare at least the second principal component of the first representative ECG to the second aligned component of the second representative ECG to determine whether a cardiac change occurred in the patient.

BRIEF DESCRIPTION OF THE DRAWINGS

The drawings illustrate the best mode presently contemplated of carrying out the disclosure. In the drawings.

DETAILED DESCRIPTION OF THE DRAWINGS

The inventors recognize that there is significant variability between various ECG recordings for the same patient because multiple factors introduce waveform differences. For example, slight variations in lead placement and/or patient positioning can sometimes result in significant differences in the waveforms recorded by an ECG monitor. These differences make it difficult to compare ECG waveforms to one another, thus making it difficult to interpret whether clinically significant cardiac changes occur in a patient that may be evident in serial ECG recordings. Accordingly, the present inventors recognize a long felt need for an apparatus and method for reducing sources of variability from serial ECG waveforms and normalizing ECG waveforms so that they may be visually and numerically compared. Furthermore, the present inventors recognize that it is beneficial to present serial ECG waveform comparisons in a format that clinicians are familiar with, which is the standard ECG waveform format. Motivated by the recognition of this problem, the inventors developed the apparatus and method of analyzing ECG waveforms disclosed herein.

Figure 1:
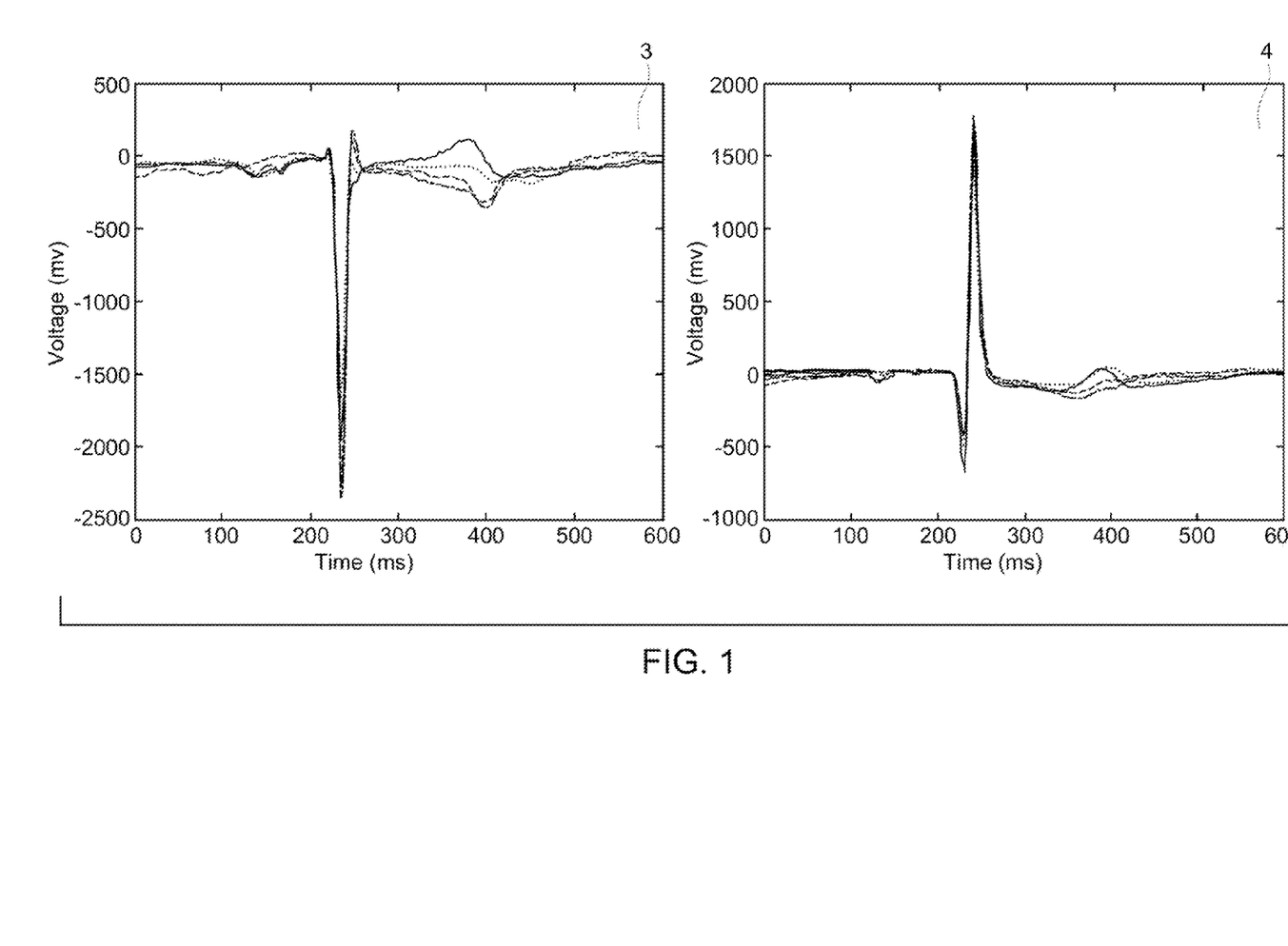
FIG. 1 depicts a graph presenting first components and a graph presenting second components of four ECG recordings of a patient prepared according to the methods disclosed herein.

FIG. 1 depicts first and second components calculated from four separate ECG recordings. As will be described more thoroughly herein, waveforms from each of the four ECGs are aligned according to their depolarization portions in the region of the QRS complex. Such alignment allows direct comparison of a patient's heartbeat as recorded on four different occasions. Furthermore, the calculation of a depolarization subspace from the ECG depolarization alignment as described herein enables differentiation of certain primary repolarization changes from secondary repolarization abnormalities. Serial ECG recordings may be compared according to the method 1 of analyzing ECG data disclosed herein to detect cardiac abnormalities including myocardial infarction, myocardial ischemia, conduction defects (including left bundle branch block, right bundle branch block, incomplete and indeterminate bundle branch blocks, and incomplete and indeterminate bundle branch blocks), ventricular hypertrophy (including but not limited to both left ventricular hypertrophy and right ventricular hypertrophy), acute pericarditis, and ion channelopathies.

In FIG. 1, graph 3 depicts the first primary component of a first ECG and first aligned components of three subsequent ECG recordings. The first primary and aligned components each depict a single representative heartbeat of a patient measured along a first primary component axis calculated according to the methods disclosed herein. The first primary and first aligned components are overlaid on top of one another with respect to time, which is depicted in milliseconds. Graph 4 depicts the second primary and second aligned components from the same four serial ECG recordings. More specifically, graph 4 depicts a second primary component and three aligned components overlaid on top of one another with respect to time. Each of the second primary and aligned components depict the representative heartbeat of the patient depicted along a second primary component axis calculated according to the method disclosed herein. The second primary component axis is perpendicular to the first primary component axis and thus represents independent electrical activity than that captured along the first primary component axis (see FIG. 4). In some embodiments, and as is described herein, a third set of primary and aligned components may also be calculated and depicted along a third primary component axis, wherein the third primary component axis is perpendicular to the first primary component axis and the second primary component axis.

Figure 6:
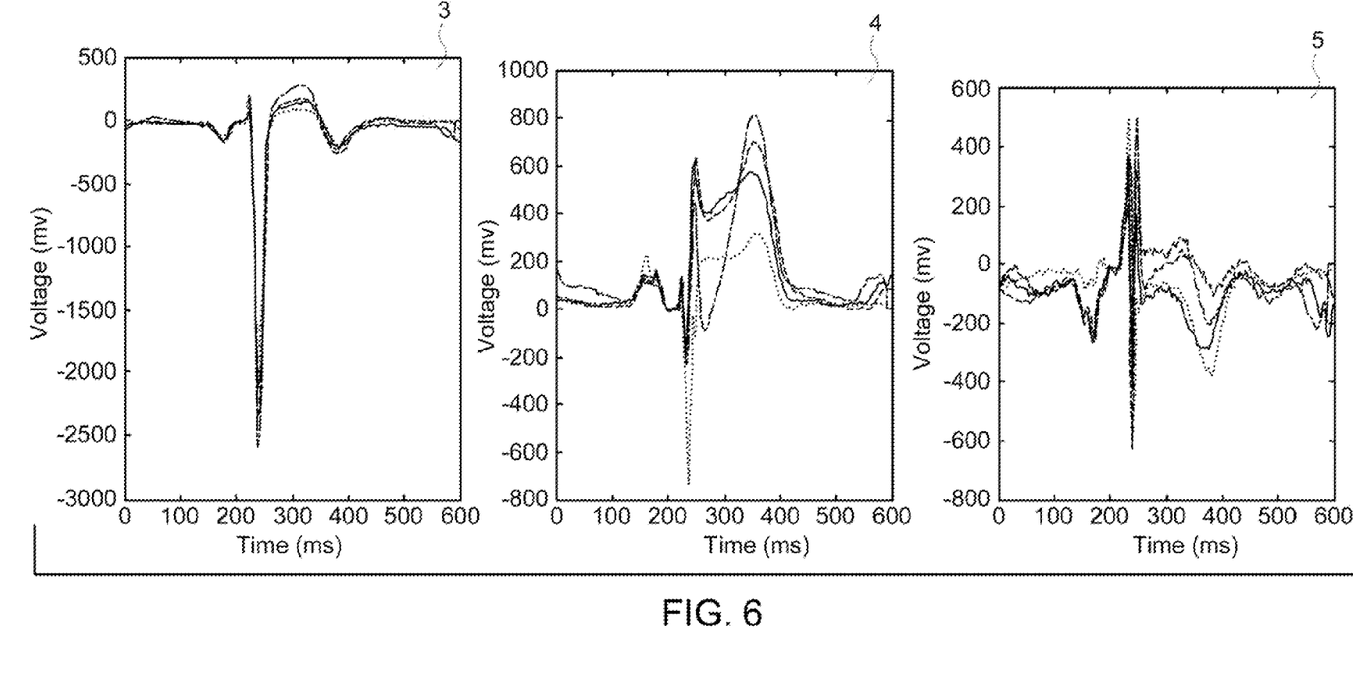
FIG. 6 depicts three graphs presenting corresponding principal components and aligned components.

The four serial ECG recordings that resulted in the calculation of the first and second components in FIG. 1 were recorded from a patient with a normal and healthy heart. Thus, the first components shown in graph 3 generally fall into alignment with one another, as do the second components shown in graph 4. By comparison, FIG. 6 presents first, second, and third primary and aligned components of ECGs taken from a patient with an acute myocardial infarction. As is evident, the primary and aligned components derived from the ECGs of the patient with cardiac disease do not align as well as those for the patient with a normal heart. In the example of FIG. 6, a clinically significant change in the ECG components is primarily seen in the second graph 4, which can be associated with a primary repolarization change, independent of the depolarization vector direction, due to the patient's acute myocardial infarction. Namely, graph 4 demonstrates a significant change between the second primary component and the second aligned components indicating that a significant cardiac change occurred in the patient between the ECG recording associated with the second primary component and the ECG recordings associated with the second aligned components.

Such a primary repolarization change reflected in ST-T segment morphology changes, like that seen in graph 4 of FIG. 6, may be due to a myocardial infarction. Other exemplary cardiac abnormalities detectable as primary repolarization changes may include, but are not limited to, myocardial ischemia, congenital or drug induced ion channelopathies, acute pericarditis. A significant change detected by comparing the first primary component and the first aligned components may indicate that a primary depolarization change and secondary repolarization change have occurred in the patient's heart. Examples of cardiac abnormalities involving a primary depolarization changes and secondary repolarization changes include, without limitation, left bundle branch block, right bundle branch block, incomplete and indeterminate bundle branch blocks, and incomplete and indeterminate bundle branch blocks, ventricular hypertrophy (including but not limited to both left ventricular hypertrophy and right ventricular hypertrophy).

Figure 2:
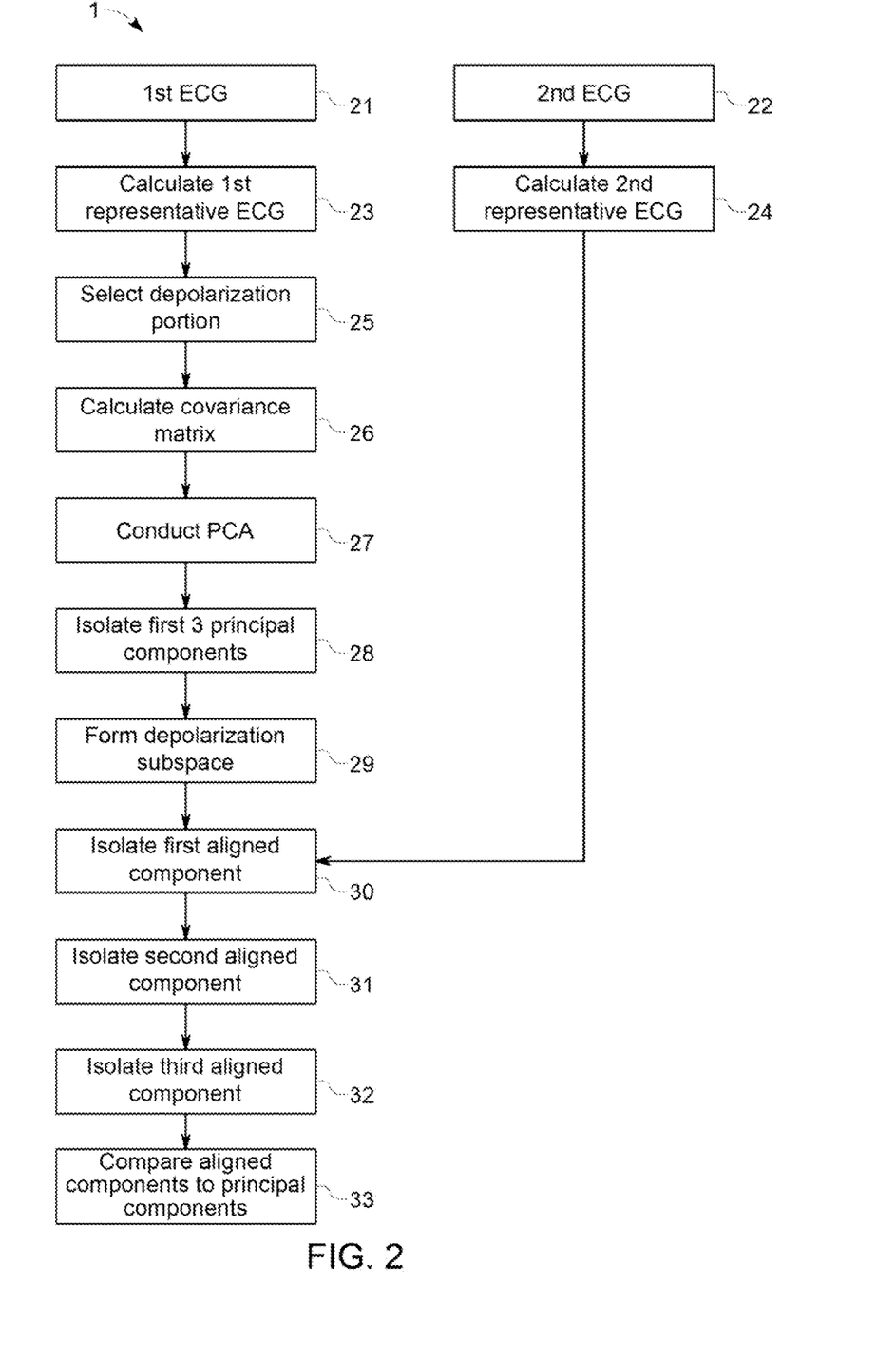
FIG. 2 depicts an exemplary method of analyzing ECG data.
Figure 3:
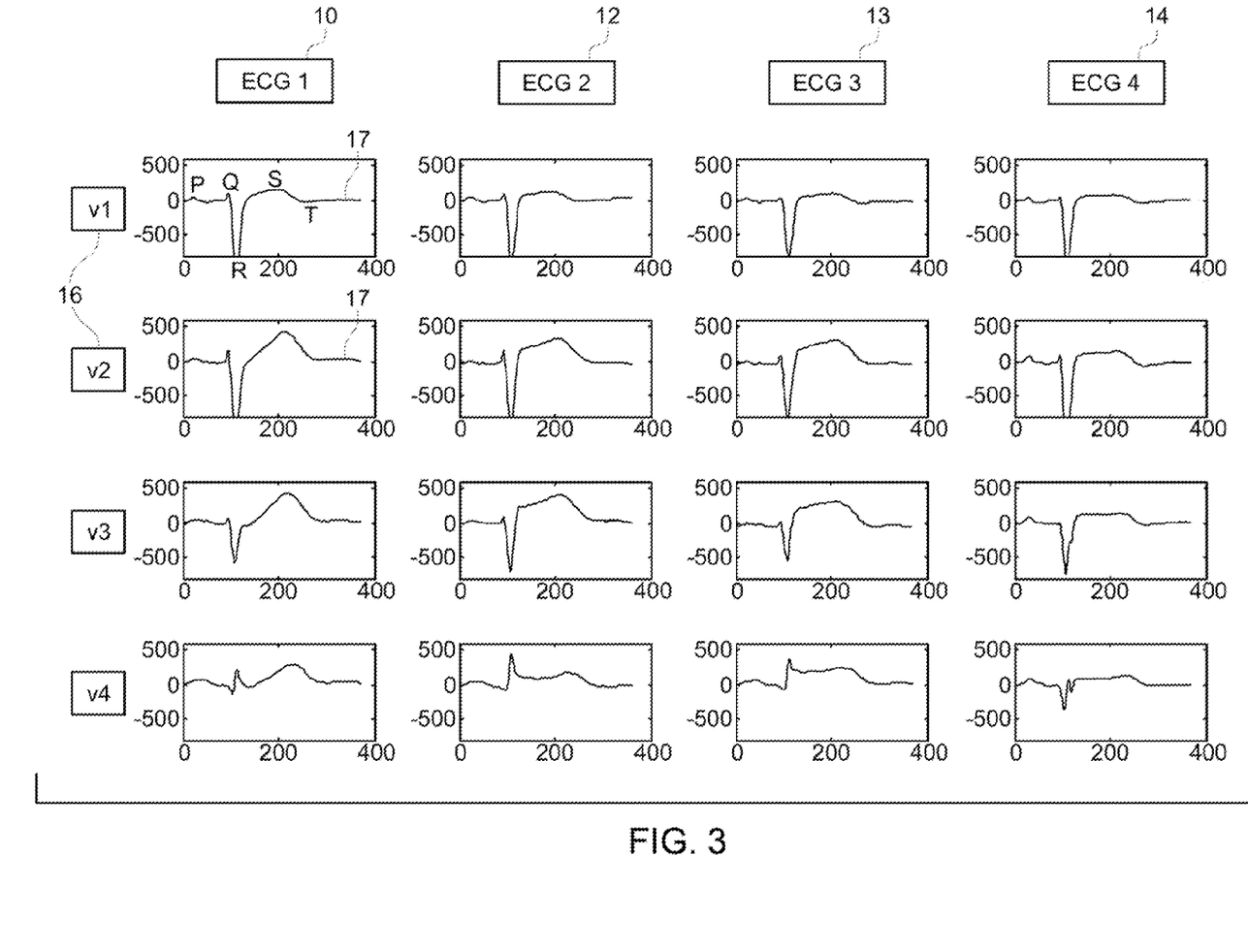
FIG. 3 depicts four representative ECGs of a patient.

FIG. 2 depicts an exemplary embodiment of a method 1 of analyzing ECG data. The first ECG recording is received at step 21. The first ECG recording may be, for example, raw or filtered data taken by a standard 12-lead ECG arrangement on a patient. In other embodiments, other ECG lead arrangements may be used, such as a 15-lead ECG arrangement, derived 12 lead arrangements where a smaller set of electrodes is used to synthesize the standard 12 lead ECG, Frank X, Y, Z leads, Bipolar X, Y, Z leads, or any connection with more than 2 actual leads. A first representative ECG is then calculated at step 23 based on the first ECG data supplied at step 21. The first representative ECG is one or more waveforms representing a heartbeat of the patient. For example, FIG. 3 depicts four representative ECGs, including a first representative ECG 10, a second representative ECG 12, a third representative ECG 13, and a fourth representative ECG 14. In the embodiment depicted in FIG. 3, each representative ECG 10, 12, 13, 14 is comprised of four representative waveforms 17. Each representative waveform 17 represents a heartbeat of a patient and is calculated based on ECG data from one ECG lead 16. For example, the four exemplary representative waveforms 17 are calculated based on the V1, V2, V3, and V4 ECG leads 16, respectively, which are recorded from a patient using a standard 12-lead ECG arrangement. In other embodiments, each representative ECG 10, 12, 13, 14 may be comprised of any number of four or more representative waveforms 17. For example, each representative ECG 10, 12, 13, 14 may comprise 12 representative waveforms 17, each calculated based on data gathered from one lead of a standard 12 lead ECG. The data from each lead 16 may include multiple waveforms representing heartbeats of a patient. For example, a standard diagnostic ECG may comprise ten seconds of ECG data recorded from each of 12 leads. The representative waveform 17 may be calculated by any of a number of methods for formulating a waveform depicting a single representative heartbeat. Each representative waveform 17 may be, for example, an average or median waveform determined based on the ECG data from a lead. For example, a representative waveform may be calculated by computing a mathematical average or a weighted average of individual beat waveforms in ECG data. In another embodiment, the representative waveform 17 may be determined by selecting a median of multiple individual beat waveforms recorded in one lead 16. In still other embodiments, the representative waveform 17 may be calculated by other means or may simply be a selected waveform of one heartbeat recorded from a patient.

Referring, again to FIG. 2, a depolarization portion of the representative ECG is selected at step 25, which is the portion of the waveforms upon which the alignment is calculated. More specifically, and as will be made apparent herein, the selected depolarization portion provides the basis for calculating the depolarization subspace. The depolarization portion may be any portion of the representative ECG associated with the depolarization of the patient's heart. In the example depicted in FIG. 3, the selected portion of the representative ECG may be the QRS complex of each representative waveform 17. In other embodiments, the selected portion representing depolarization may be a subsection of the QRS complex of the representative waveform 17. For example, the QR section or the RS section of the QRS complex may be selected. Alternatively, the first 40 millisecond or the last 40 millisecond portion of QRS complex may be selected.

Figure 4:
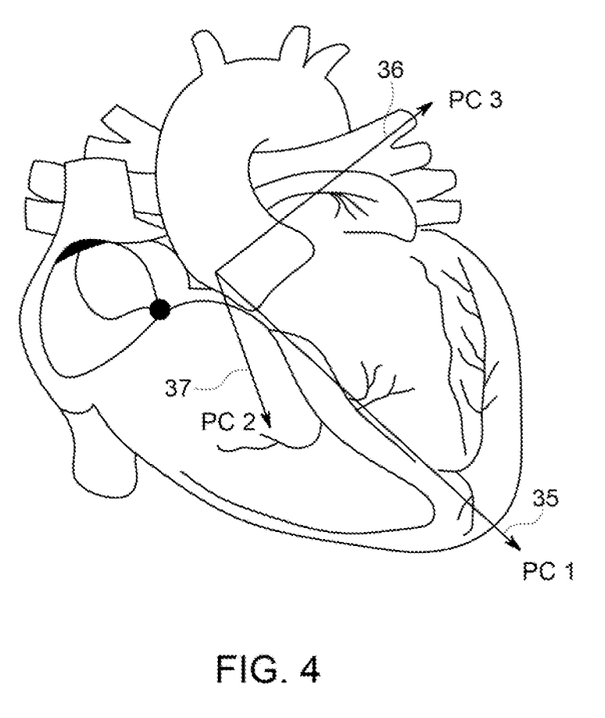
FIG. 4 depicts exemplary vectors of a first three principal components projected onto a depiction of a human heart.

At step 26, the selected portion of the representative ECG is used to calculate a covariance matrix. The covariance matrix generalizes the notion of variance to multiple dimensions. Here, the covariance matrix is applied to determine variance in electrical activity across the patient's heart in multiple dimensions during the heartbeat represented in the representative ECG 10, 12, 13, 14. Then, at step 27, a principal component analysis is conducted of the covariance matrix calculated at step 26 to rank the vectors in descending order, with the largest variation as the first vector, the second largest variation as the second vector, and so on. As is known in the art, principal component analysis (PCA) is a statistical procedure that uses an orthogonal transformation to convert a set of observations of possibly correlated variables in multiple dimensions, such as a set of representative waveforms depicting a patient's heartbeat, into a set of values of linearly uncorrelated variables called principal vectors. The number of principal components is less than or equal to original number of vectors. Thus, in order to get the three principal components as required by the method described herein, representative waveform 17 from at least three ECG leads 16 are used. This transformation is defined in such a way that the first principal component has the largest possible variance—i.e., accounts for as must of the variability in the data as possible. Each succeeding, component in turn has the next highest variance after subtracting the higher ranked variances under the constraint that it is orthogonal to, or uncorrelated with, the preceding components. Thus, the second principal component is the component, or vector, having the most energy out of the possible vectors that are perpendicular to the vector of the first principal component. Likewise, the third principal component is the component with the most energy along an axis that is perpendicular to both the first principal component and the second principal component. FIG. 4 provides an exemplary demonstration of a first principal component axis 35, a second principal component axis 36, and a third principal component axis 37 projected onto a picture of a patient's heart. The three orthogonal axes 35, 36, and 37 define a 3 dimensional space which is referred to herein as a depolarization subspace. To provide further exemplification, the graphs 3 in FIGS. 1 and 6 represent primary and aligned components along the first principal component axis 35 where the energy in the aligned depolarization portions of the waveforms is the highest. Graphs 4 in FIGS. 1 and 6 depict the electrical activity of the patient's heartbeat along the second principal component axis 36, which is perpendicular to the first principal component axis 35. Graph 5 in FIG. 6 depicts the electrical activity of the patient's heartbeat along the third principal component axis 36. Notably, the waveforms in graphs 3 have more energy than those in graphs 4 (FIGS. 1 and 6), and the waveforms in graph 4 have more energy than the waveforms in graph 5 (FIG. 6).

Figure 5:
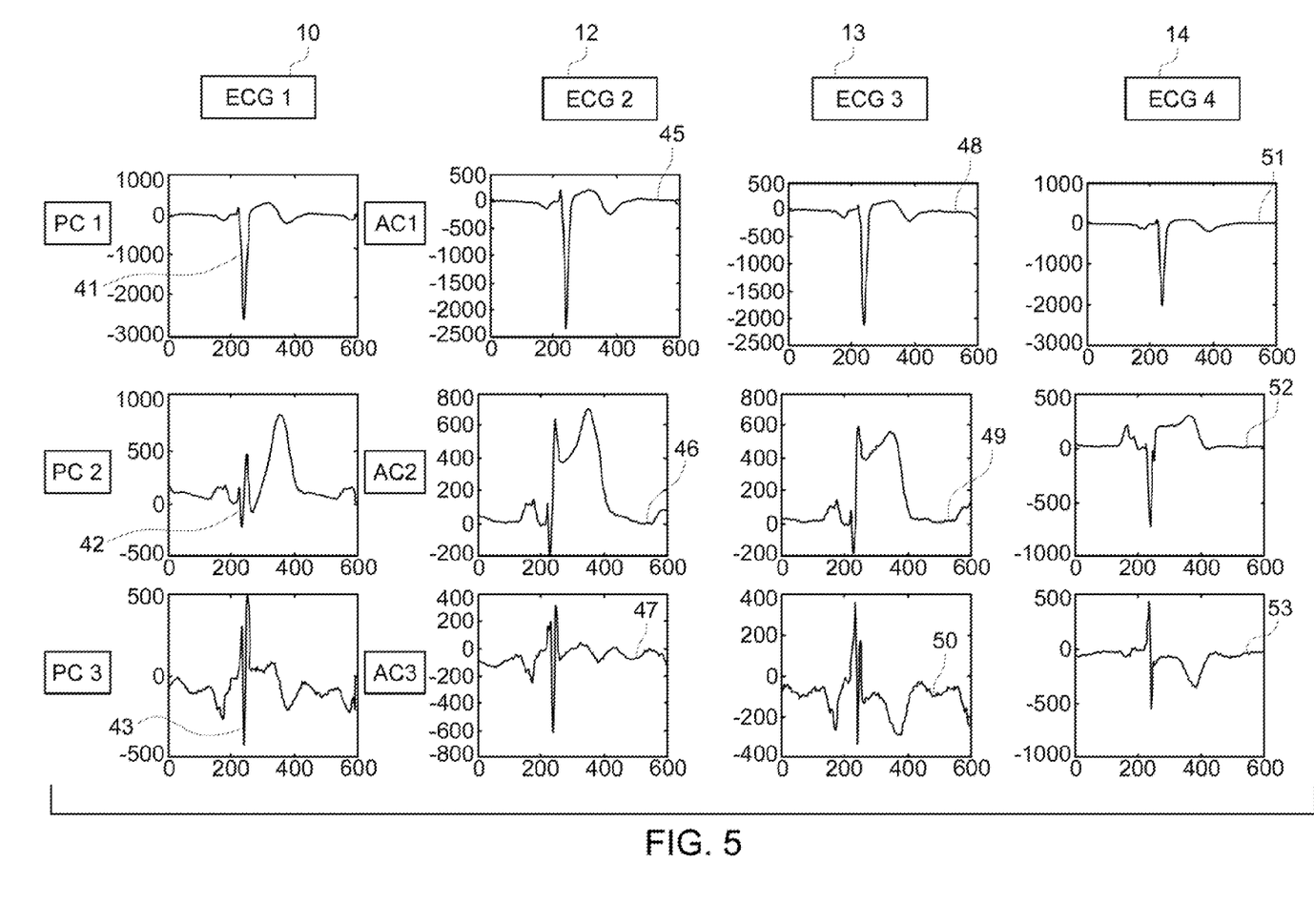
FIG. 5 depicts an exemplary first three principal components for a first ECG and a first three aligned components for three subsequent ECGs.

At step 28 in the method of FIG. 2, the first three principal components are isolated from the PCA conducted at step 27. Referring now to FIG. 5, an exemplary first three principal components calculated based on the first representative ECG 10 are provided in the left hand column. The first representative ECG 10 is exemplified as four representative waveforms 17. In other embodiments, the first representative ECG may be twelve representative waveforms correlating to a standard 12-lead ECG. In such an embodiment, the steps of calculating a covariance matrix 26 and conducting the PCA 27 are employed so that three principal components result from the twelve representative waveforms. Namely, in embodiments where more than 4 representative waveforms 17 are used, the waveforms are included as additional vectors used in the calculation of the covariance matrix. The first principal component 41 represents the most energy in the aligned depolarization portion and thus has the highest magnitude. Then, the second principal component 42 represents the greatest amount of energy in a direction that is perpendicular to the axis of the component 41. The magnitude of the second principal component 42 is less than that of the first principal component 41. The third principal component 43, intern, has the most amount of energy in a direction that is perpendicular to the axis of the second principal component 42. The magnitude of the third principal component 43 is less than that of the second principal component 42.

At step 29 a depolarization subspace is formed as the orthogonal axes of the first principal component vector (axis 35), the second principal component vector (axis 36), and the third principal component vector (axis 37). These three axes define a space that all subsequent ECGs will be projected into in order to align and compare the serial ECG recordings.

A second representative ECG is calculated at step 24 based on the second ECG received at step 22. The second representative ECG is then projected into the depolarization subspace created at steps 25-29. Thereby, at step 30, a first aligned component is isolated, wherein the first aligned component is the portion of the second representative ECG that is on the same axis as the first principal component of the first ECG. Likewise, at step 31, a second aligned component is isolated from the second representative ECG, wherein the second aligned component is the component of the second representative ECG 12 along the axis of the second principal component 42. The third aligned component is isolated at step 32. For example, the third aligned component 47 is the component of the second representative ECG 12 along the same axis as the third principal component 43 of the first representative ECG 10. The concept of aligned components is exemplified in FIG. 5, which depicts exemplary first aligned components 45, 48, and 51, second aligned components 46, 49, and 52, and third aligned components 47, 50, and 53.

The method steps 22, 24 and 30-32 describe the method by which the second representative ECG 12 is projected into the depolarization subspace defined by the principal components 41, 42, and 43 of the first ECG 10. The same steps can be repeated for any number of additional ECG recordings and representative ECGs. In the example depicted in FIGS. 3, 5 and 6, four serial ECG recordings are calculated into representative ECGs and then projected into the same depolarization subspace so that they may be compared. Namely, the third representative ECG 14 is projected into the depolarization subspace to isolate a first aligned component 48, a second aligned component 49, and a third aligned component 50. Likewise, a fourth representative ECG 14 is projected into the depolarization subspace resulting in a first aligned component 51, a second aligned component 52, and a third aligned component 53.

At step 33, which is the final step of the exemplary method 1 depicted in FIG. 2, the aligned components are compared to their respective corresponding principal components. FIG. 6 depicts one exemplary comparison. A first graph 3 provides the first principal component 41 of ECG 10 plotted with respect to time and voltage along with the first aligned component 45 of the second representative ECG 12, the first aligned component 48 of the third representative ECG 13 and the first aligned component 51 of the fourth representative ECG 14. The second graph 4 depicts the second principal component 42 of the first representative ECG 10 plotted along with the second aligned component 46 of the second representative ECG 12, the second aligned component 49 of the third representative ECG 13, and the second aligned component 52 of the fourth representative ECG 14. Similarly, the third graph 5 presents the third principal component 43 along with the third aligned components 47, 50, and 53. In this way, the primary components 41, 42, 43 can be compared to the corresponding aligned components. FIG. 1 provides a similar comparison of different ECG data.

Alternatively or in addition to displaying the principal components and aligned components on the same graph, a morphology of the aligned component waveforms may be compared to a morphology of the principal component waveforms to determine whether a clinically significant change has occurred in the patient's heart between the first ECG and any subsequent ECG. In one embodiment, an adaptive algorithm, such as a neural network, may be trained to determine whether a clinically significant change exists between a principal component and any aligned component (s). The adaptive algorithm may be trained using training data comprising exemplary ECG waveforms, including exemplary primary components and aligned components, along with corresponding information regarding the existence of clinically significant changes and/or diagnoses. In another embodiment, the primary components and aligned components of ECG recordings may be compared and assessed using a set of criteria developed via a statistical method or function applied to a set of sample data to determine optimal criterion points for differentiating between normal and significant changes.

The principal component and corresponding aligned components may be compared based on a set of features. The features upon which the comparisons are made may be any features for detecting a clinically significant change. Such features may include, but are not limited to, ST-T wave amplitude, ST-T wave slope, ST-T wave shape, QRS deflections, QRS duration, QT interval, heart rate corrected QT interval, and P-QRS-T axes. Further, the features upon which the waveforms are compared may be defined based on the results of an initial assessment of the differences between the primary components and one or more of the aligned components. For example, referring to FIGS. 5 and 6, the feature set upon which the primary and aligned components are compared may be established based on the differences between the second primary component 42 and the second aligned components 46, 49, 52. These differences are evident in graph 4 of FIG. 6. Based on the significant differences noted in the second primary and aligned components, it may be desirable to compare the primary and aligned components based on features of the ST and T sections of the waveforms. This may include ST-T wave amplitudes and durations, T wave notches, T wave flatness, U wave amplitude, as well as the QRS-T angle.

Figure 7:
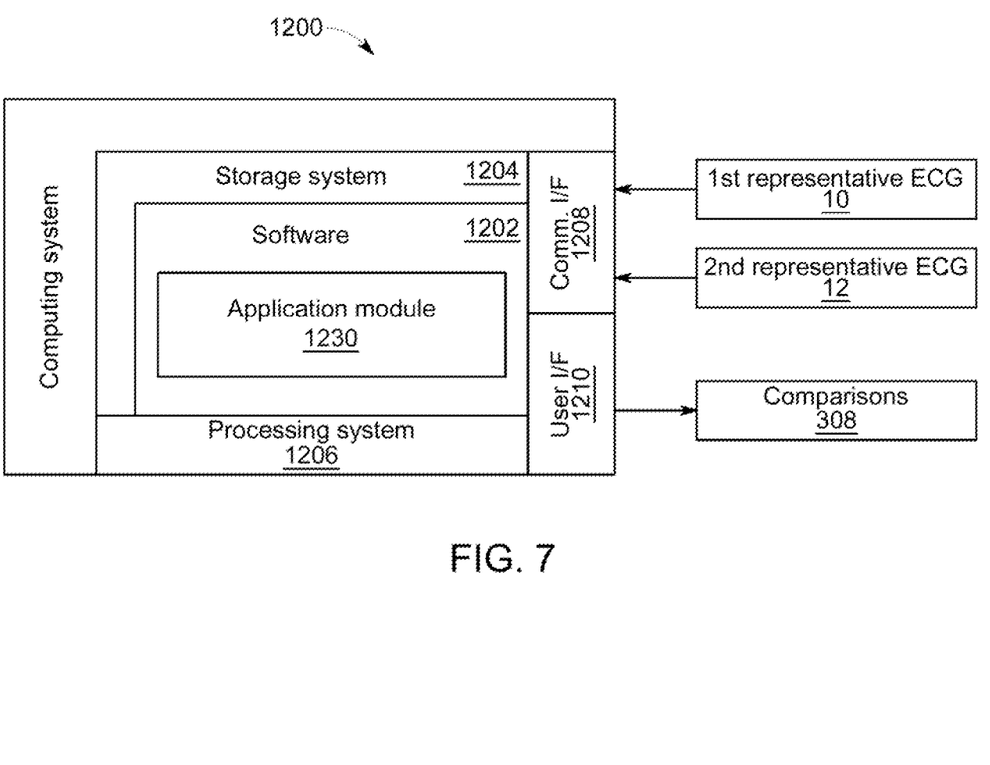
FIG. 7 depicts an exemplary system diagram for executing a computer program product for detecting a cardiac change in a patient.

FIG. 7 is a system diagram of an exemplary embodiment of a system 1200 for implementing a computer program product for analyzing ECG data. The application module 1230, which is a computer program product, may include or be broken into submodules to execute the methods described herein, including a first program product portion configured to form a depolarization subspace, a second program product portion configured to project subsequent representative ECG into that depolarization subspace, and a third program product portion configured to compare the principal components to the aligned components. The system 1200 is generally a computing system that includes a processing system 1206, storage system 1204, software 1202, communication interface 1208 and a user interface 1210. The processing system 1206 loads and executes software 1202 from the storage system 1204, including application module 1230. When executed by the computing system 1200, application module 1230 directs the processing system 1206 to operate as described in herein in further detail, including execution of a first, second, and third program product portions.

Although the computing system 1200 as depicted in FIG. 7 includes one software module in the present example, it should be understood that one or more modules could provide the same operation. Similarly, while description as provided herein refers to a computing system 1200 and a processing system 1206, it is to be recognized that implementations of such systems can be performed using one or more processors, which may be communicatively connected, and such implementations are considered to be within the scope of the description.

The processing system 1206 can comprise a microprocessor and other circuitry that retrieves and executes software 1202 from storage system 1204. Processing system 1206 can be implemented within a single processing device but can also be distributed across multiple processing devices or subsystems that cooperate in executing program instructions. Examples of processing system 1206 include general purpose central processing units, application specific processors, and logic devices, as well as any other type of processing device, combinations of processing devices, or variations thereof.

The storage system 1204 can comprise any storage media readable by processing system 1206, and capable of storing software 1202. The storage system 1204 can include volatile and non-volatile, removable and non-removable media implemented in any method or technology for storage of information, such as computer readable instructions, data structures, program modules, or other data. Storage system 1204 can be implemented as a single storage device but may also be implemented across multiple storage devices or subsystems. Storage system 1204 can further include additional elements, such as a controller, capable of communicating with the processing system 1206.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination of variation thereof, or any other type of storage medium. In some implementations, the storage media can be a non-transitory storage media. In some implementations, at least a portion of the storage media may be transitory. It should be understood that in no case is the storage media a propagated signal.

User interface 1210 can include a mouse, a keyboard, a voice input device, a touch input device for receiving a gesture from a user, a motion input device for detecting non-touch gestures and other motions by a user, and other comparable input devices and associated processing elements capable of receiving user input from a user. Output devices such as a video display or graphical display can display an interface further associated with embodiments of the system and method as disclosed herein. Speakers, printers, haptic devices and other types of output devices may also be included in the user interface 1210. As disclosed in detail herein, the user interface 1210 operates to output the comparisons 308, which are outputs related to the comparison of one or more aligned components of ECG waveforms such as second representative ECG 12) to a corresponding principal component of an ECG waveform for the same patient (such as first representative ECG 10).

As described in further detail herein, the computing system 1200 receives at least a first representative ECG 10 and a second representative ECG 12. First and second representative ECGs 10 and 12 may be, for example, representative waveforms calculated from a filtered or unfiltered digital ECG recording comprising cardiac data recorded from four or more leads. The first representative ECG 10 and the second representative ECG 12 may be retrieved from a storage location in storage system 1204, for example. In another embodiment, the computing system 1200 may retrieve a first ECG data and a second ECG data and calculate a representative ECG as described herein. For example, the ECG data may be retrieved from a storage location in storage system 1204, from an external storage system (such as an ECG data repository or electronic medical record system), or from an ECG acquisition device.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of analyzing electrocardiograph (ECG) data, the method comprising:
   receiving a first representative ECG of a patient;
   isolating a first principal component , a second principal component, and a third principal component of the first representative ECG by
      selecting a portion of the first representative ECG relating to depolarization;
      calculating a covariance matrix based on the portion of the first representative ECG;
      conducting a principal component analysis of the covariance matrix; and
      selecting the first component of the principal component analysis as the first principal component, the second component of the principal component analysis as the second principal component, and the third component of the principal component analysis as the third principal component; and
   forming a depolarization subspace based on the first principal component, the second principal component, and the third principal component of the first representative ECG.

2. The method of claim 1 further comprising receiving a second representative ECG of the patient;
   projecting the second representative ECG to the depolarization subspace to isolate at least a first aligned component and a second aligned component of the second representative ECG, wherein the first aligned component is on the same axis as the first principal component and the second aligned component is on the same axis as the second principal component; and
   comparing the second principal component of the first representative ECG to the second aligned component of the second representative ECG.

3. The method of claim 2 further comprising comparing the first principal components of the first representative ECG to the first aligned component of the second representative ECG.

4. The method of claim 1, wherein the first representative ECG is at least 4 representative waveforms representing a heart beat of a patient, wherein each representative waveform is calculated based on ECG data from one ECG lead.

5. The method of claim 4, wherein the first representative ECG is 12 representative waveforms, wherein each representative waveform is an average of multiple waveforms recorded from one lead of a standard 12 lead ECG or a median of multiple waveforms recorded from one lead of a standard 12 lead ECG.

6. The method of claim 4, wherein the portion of the first representative ECG relating to depolarization is the QRS segment of each of the representative waveforms.

7. The method of claim 4, wherein the portion of the first representative ECG relating to depolarization is a portion of the QRS segment of each of the representative waveforms.

8. The method of claim 2, wherein the step of comparing includes displaying the second principal component of the first representative ECG and the second aligned component of the second representative ECG together on a graph.

9. The method of claim 3, wherein the step of comparing includes displaying the first principal component of the first representative ECG and the first aligned component of the second representative ECG together on a first graph, and displaying the second principal component of the first representative ECG and the second aligned component of the second representative ECG together on a second graph.

10. The method of claim 2, wherein the step of comparing includes comparing a morphology of the second principal component of the first representative ECG to a morphology of the second aligned component of the second representative ECG to determine whether a significant cardiac change occurred in the patient.

11. A method of comparing serial electrocardiograph (ECG) data, the method comprising:
   forming a depolarization subspace based on a first principal component, a second principal component, and a third principal component of a first representative ECG by
      calculating a covariance matrix based on a portion of the first representative ECG relating to depolarization of a patient's heart;
      conducting a principal component analysis of the covariance matrix; and selecting the first component of the principal component analysis as the first principal component, the second component of the principal component analysis as the second principal component, and the third component of the principal component analysis as the third principal component; and projecting a second representative ECG to the depolarization subspace to isolate at least a first aligned component and a second aligned component of the second representative ECG;

wherein the second representative ECG is based on ECG data recorded from the patient at a different time than the first representative ECG;

wherein the first aligned component is on the same axis as the first principal component and the second aligned component is on the same axis as the second principal component.

12. The method of claim 11, wherein the first representative ECG is at least 4 representative waveforms representing a heart beat of a patient, wherein each representative waveform is calculated based on ECG data from one ECG lead; and wherein the portion of the first representative ECG relating to depolarization is at least a portion of the QRS segment of each of the representative waveforms.

13. The method of claim 11 further comprising comparing the second principal component of the first representative ECG to the second aligned component of the second representative ECG to determine whether a significant cardiac change occurred in the patient.

14. The method of claim 11 further comprising comparing the first principal component of the first representative ECG to the first aligned component of the second representative ECG and comparing the second principal component of the first representative ECG to the second aligned component of the second representative ECG to determine whether a significant cardiac change occurred in the patient.

15. The method of claim 13 further comprising defining a set of features upon which the first principal component of the first representative ECG is compared to the first aligned component of the second representative ECG and the second principal component of the first representative ECG is compared to the second aligned component of the second representative ECG.

16. The method of claim 15 wherein the set of features includes at least one of an ST-T wave amplitude, ST-T wave slope, ST-T wave shape, QRS deflections, QRS duration, QT interval, heart rate corrected QT interval, and P-QRS-T axes.

17. The method of claim 15 wherein the set of features is defined based on a difference between a morphology of the second principal component of the first representative ECG and a morphology of the second aligned component of the second representative ECG.

18. A computer program product for detecting a cardiac change in a patient, the system comprising a first program product portion configured to form a depolarization subspace based on a first principal component, a second principal component, and a third principal component of a first representative ECG by
calculating a covariance matrix based on a portion of the first representative ECG relating to depolarization of a patient's heart;
conducting a principal component analysis of the covariance matrix; and
selecting the first component of the principal component analysis as the first principal component, the second component of the principal component analysis as the second principal component, and the third component of the principal component analysis as the third principal component;

a second program product portion configured to project a second representative ECG to the depolarization subspace to isolate at least a first aligned component and a second aligned component of the second representative ECG, wherein the first aligned component is on the same axis as the first principal component and the second aligned component is on the same axis as the second principal component; and a third program product portion configured to compare at least the second principal component of the first representative ECG to the second aligned component of the second representative ECG to determine whether a cardiac change occurred in the patient.

19. The computer program product of claim 18, wherein the first representative ECG is at least 4 representative waveforms representing a heart beat of a patient, wherein each representative waveform is calculated based on ECG data from one ECG lead; and wherein the portion of the first representative ECG relating to depolarization is at least a portion of the QRS segment of each of the representative waveforms.

20. The computer program product of claim 18, further comprising defining a set of features upon which the second principal component of the first representative ECG is compared to the second aligned component of the second representative ECG;

wherein the set of features is at least one of an ST-T wave amplitude, ST-T wave slope, ST-T wave shape, QRS deflections, QRS duration, QT interval, heart rate corrected QT interval, and P-QRS-T axes and is defined based on a difference between a morphology of the second principal component of the first representative ECG and a morphology of the second aligned component of the second representative ECG.

* * * * *